United States Patent
Maitre et al.

[11] Patent Number: 6,015,466
[45] Date of Patent: Jan. 18, 2000

[54] MICROCRYSTALLINE SUGARS OR SUGAR-ALCOHOLS; METHOD FOR PREPARING THE SAME

[75] Inventors: Jean-Paul Maitre, Marennes; Julio Mentech, Lyons; Sylvie Reynaud, Villeurbanne; Emile Wong, Neyron, all of France

[73] Assignee: Eridania Beghin-Say, Thumeries, France

[21] Appl. No.: 09/077,748

[22] PCT Filed: Dec. 4, 1996

[86] PCT No.: PCT/FR96/01931

§ 371 Date: Jul. 21, 1998

§ 102(e) Date: Jul. 21, 1998

[87] PCT Pub. No.: WO97/21838

PCT Pub. Date: Jun. 19, 1997

[30] Foreign Application Priority Data

Dec. 11, 1995 [FR] France ................... 95 14643

[51] Int. Cl.[7] .............. C13F 1/02; C13F 3/00; C13F 1/10
[52] U.S. Cl. ............................... 127/30; 127/61
[58] Field of Search ....................... 127/30, 61

[56] References Cited

U.S. PATENT DOCUMENTS

| 3,194,682 | 7/1965 | Tippens et al. |
| 3,365,331 | 1/1968 | Miller et al. |

FOREIGN PATENT DOCUMENTS

| 0 039 123 | 11/1981 | European Pat. Off. |
| 0065775 | 1/1982 | European Pat. Off. ............. 127/61 |
| 0 052 413 | 5/1982 | European Pat. Off. |
| 0 052 919 | 6/1982 | European Pat. Off. |
| 2 244 411 | 4/1975 | France |
| 2 669 511 | 5/1992 | France |
| 1 910 752 | 11/1969 | Germany |
| 38 42 751 | 7/1990 | Germany |
| WO 91/11179 | 8/1991 | WIPO |

*Primary Examiner*—David Brunsman
*Attorney, Agent, or Firm*—Young & Thompson

[57] ABSTRACT

A composition containing sugar microcrystals is disclosed. Essentially, the crystals are uniform unbroken single crystals with a regular geometrical shape and a grain size following a Gaussian distribution of which the median is of around 20–220 μm, while the coefficient of variation is of around 20–50%, particularly 30–45%, 35–45% or 30–40%. The term "sugar" designates mono-, di- and oligosaccharides, as well as the polyols obtained by their reduction.

12 Claims, 7 Drawing Sheets

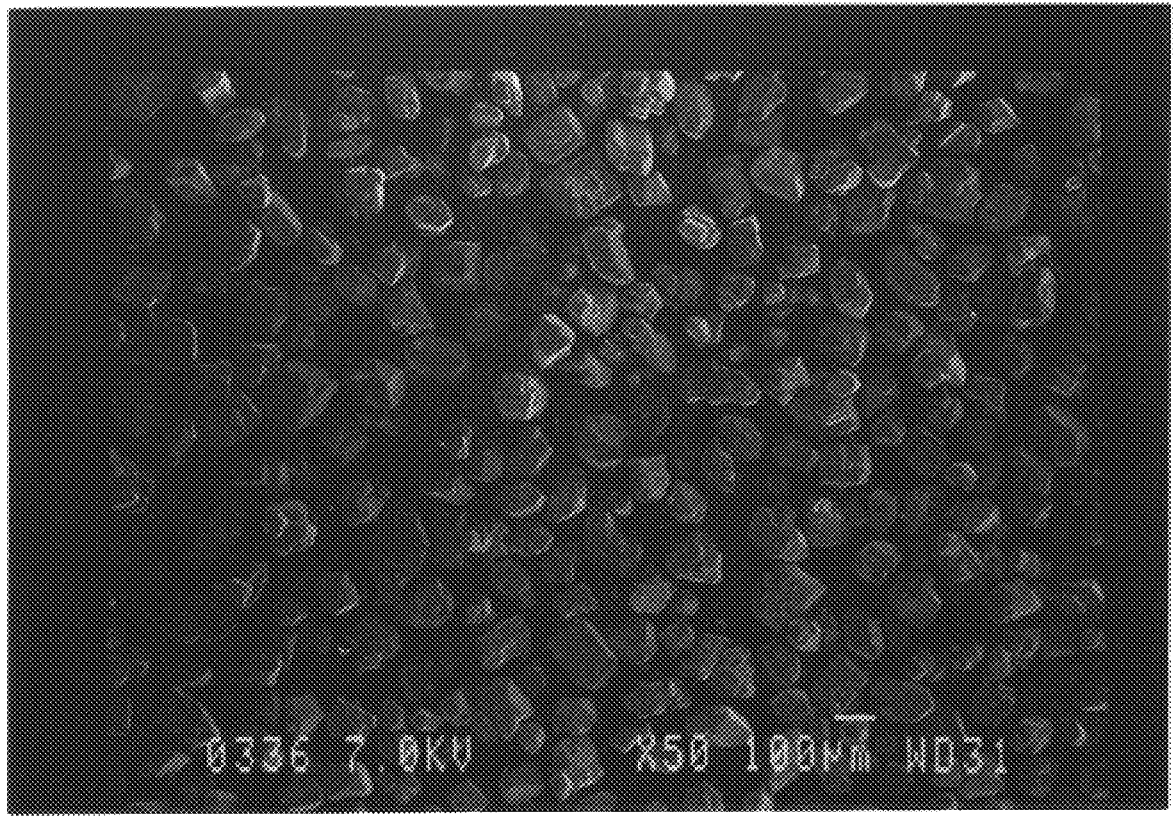
FIG_1A

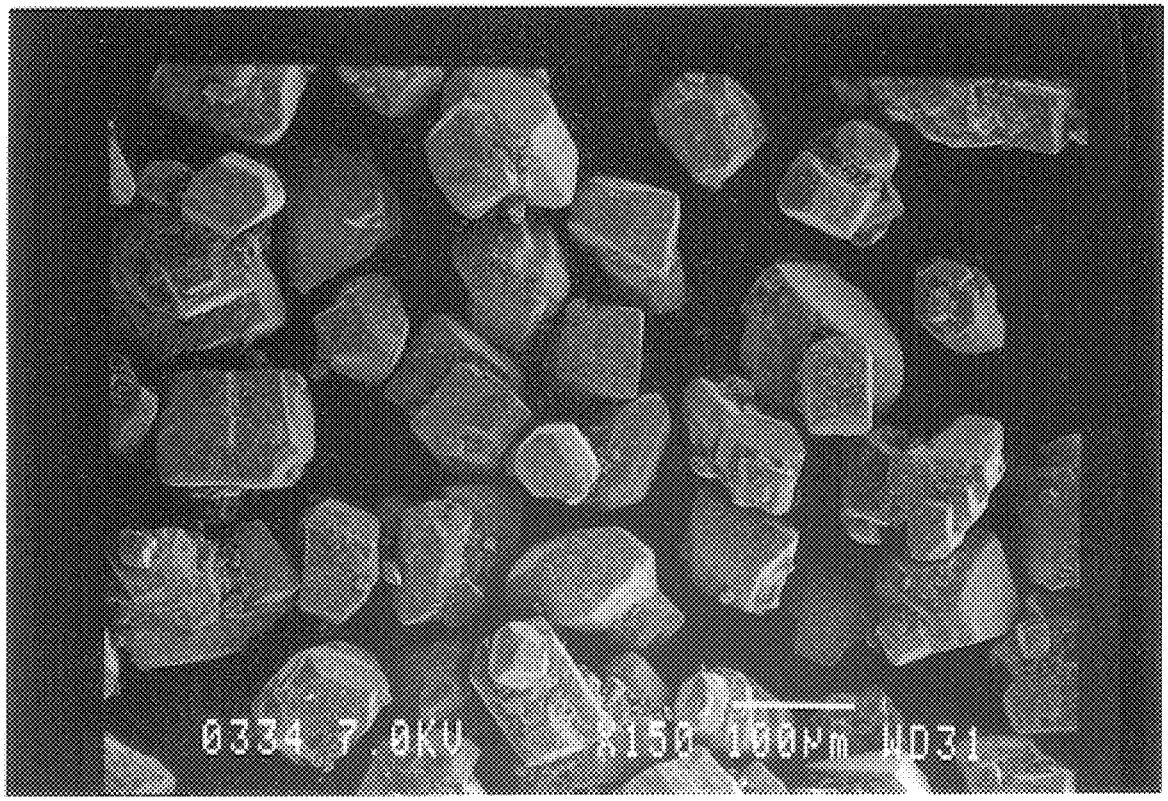
FIG_1B

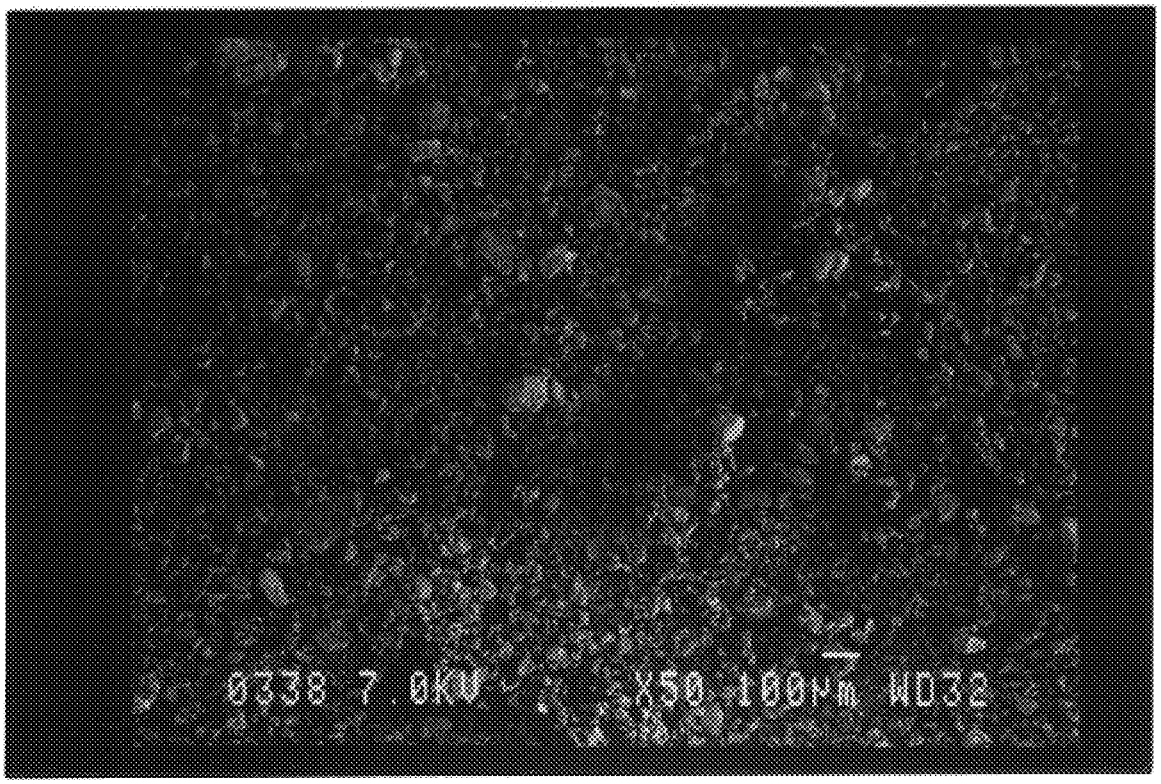
FIG_1C

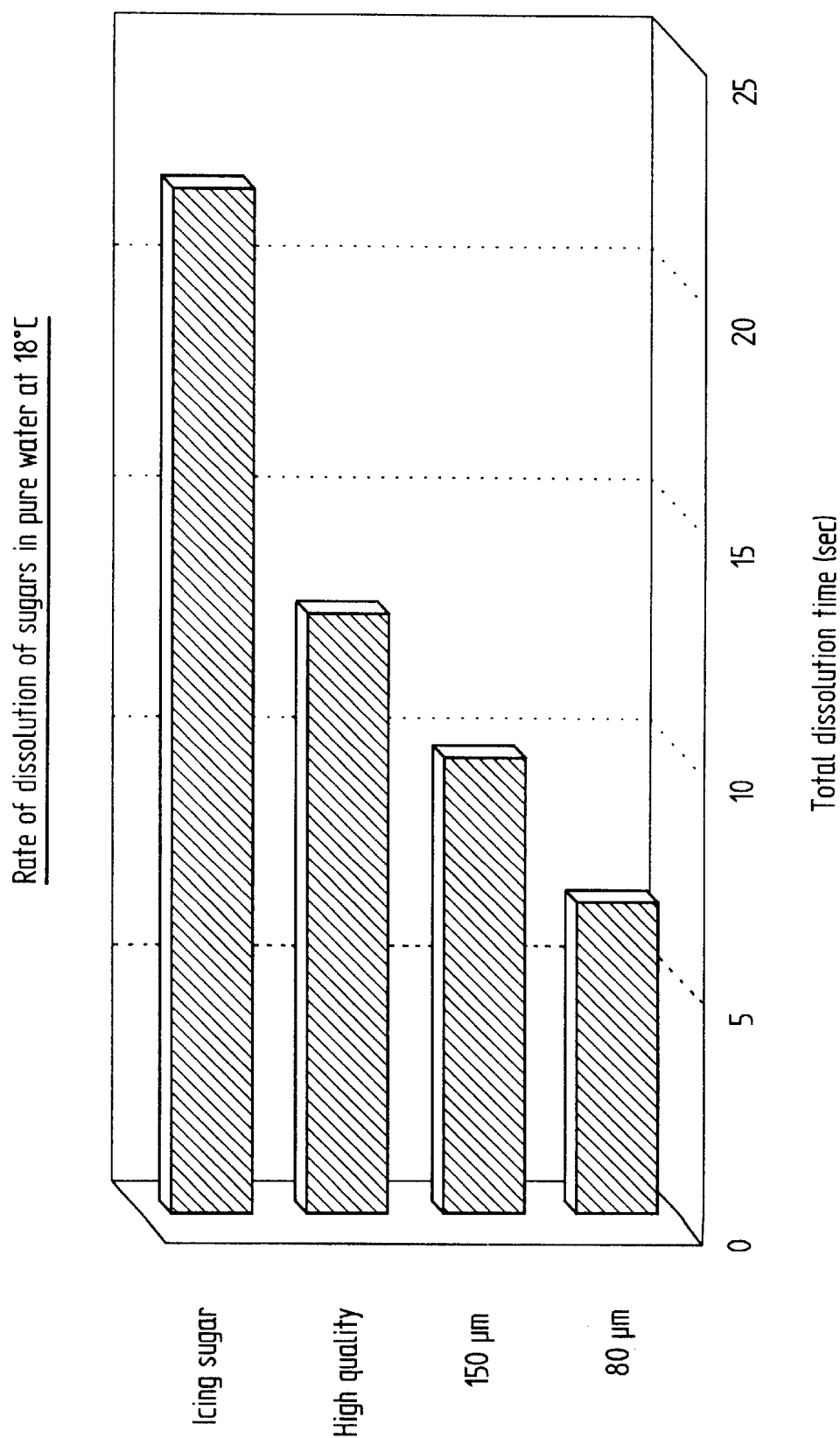
FIG._2

MICROCRYSTALLINE SUGARS OR SUGAR-ALCOHOLS; METHOD FOR PREPARING THE SAME

FIELD OF THE INVENTION

The invention concerns sugar compositions in a free-flowing, non-caking, crystalline form. The present invention relates to the field of the crystallisation of sugar, and more particularly it describes a method for obtaining compositions of crystalline sugar with a fine particle size. The invention describes a composition of crystalline sugar with a regular shape, and a fine and well-defined particle size.

BACKGROUND OF THE INVENTION

During crystallisation, the particle size distribution of the crystals depends mainly on the following processes:
nucleation,
crystal growth,
attrition,
agglomeration,
maturation of the crystals.

In order to obtain a large quantity of regular crystals with a fine particle size, it is necessary to apply a process which promotes nucleation more than crystal growth. To do this it is necessary to use appropriate means permitting good control of the crystallisation parameters.

A large quantity of sugar crystals with a regular shape and a very fine particle size cannot be obtained directly by the existing crystallisation processes. In the production of various types of sugar, a process has been developed which is better known as a conversion process. This process is used for the production of sugar in the form of a non-caking, free-flowing, granulated powder which is readily dispersed in aqueous solution. This process has been described at length in several patents.

U.S. Pat. No. 3,194,682 (Tippens et al.) describes a process using a syrup concentrated to 95–97 brix (% by weight of dry matter) at 121–129° C. which undergoes rapid cooling with vigorous agitation. This method allows the production of agglomerates of which the sugar crystals are of melting size (3–50 microns).

U.S. Pat. No. 3,365,331 (Miller et al.) describes a similar process which leads to the production of agglomerates. In this case, the crystals are obtained by beating a supersaturated syrup.

In patent EP 0 052 413, the beating process at a well controlled temperature allows heat-sensitive compounds to be incorporated in the final product.

All the processes described lead to a powder of fine-grained sugar. The granules have an irregular shape giving low density powders. As the particle size is selected by sieving, the yield of one class of powder is thus low. There is, therefore, a need to develop a process that allows the production, with good yields, of regular crystals with a fine particle size, this need being met by the present invention.

SUMMARY OF THE INVENTION

More specifically, the invention relates particularly to a composition containing sugar microcrystals, characterised in that the sugar crystals obtained have a regular shape, do not agglomerate, and their particle size follows a Gaussian distribution around a mean aperture between 20 and 220 µm, particularly 20 and 200 µm, with a coefficient of variation (CV) between 20% and 50%, or their particle size distribution is characterised by a uniformity index between 1 and 5, particularly between 2.5 and 3.5.

The particle size is determined by sieving over a series of standardised sieves (NF11-501) with a diameter of 200 mm.

The coefficient of variation (CV) is calculated by the formula:

$$CV = 100 \times \sigma / MA$$

in which $\sigma$ is the standard deviation and MA is the mean aperture.

The uniformity index is obtained by sieving the crystalline composition and calculated according to the formula:

$$\frac{\text{Particle size corresponding to 60\% of the powder passing through}}{\text{Particle size corresponding to 10\% of the powder passing through}}$$

The invention also relates to a method for obtaining a composition of microcrystalline sugar, characterised in that the crystals have a mean particle size between 20 and 220 µm, particularly 20 and 200 µm, obtained after the following steps:
a) production of a concentrated syrup,
b) reduction of pressure
c) evaporation under reduced pressure with vigorous agitation in the crystallisation zone until crystals appear,
d) stopping evaporation and maintaining agitation for a certain period,
e) resumption of evaporation and agitation until a dry product is obtained,
the temperature of the syrup being kept at 40° C. to 100° C. and particularly 70° C. to 100° C. throughout steps a) to e) described above.

This process will be referred to hereinafter as "process I".

According to an advantageous embodiment, the invention relates to a composition containing sugar microcrystals, characterised in that the crystals are essentially monocrystals that are unbroken, homogeneous with respect to one another, with a regular geometric shape, and in that
the particle size follows a Gaussian distribution the median of which is about 20 to about 220 µm and particularly about 20 µm to about 200 µm, the coefficient of variation being about 20% to about 50%, particularly about 30% to 45%, or about 35% to 45%, or about 30% to 40%, or
the particle size distribution is characterised by a uniformity index between 1 and 5, particularly between 2.5 and 3.5.

The term "sugar" designates mono-, di- and oligosaccharides, as well as the polyols obtained by the reduction thereof.

The expression "unbroken monocrystals" means that these crystals have no acute angles associated with a grinding operation.

The expression "homogeneous with respect to one another" means that these crystals have a comparable crystalline geometry.

Advantageously, the monocrystals of the compositions of the invention have a mean aperture of about 80 µm to about 120 µm.

The composition of the invention is characterised in that it has the following properties:
its rate of dissolution is about 5 to about 10, particularly about 7 to about 9 seconds, under the following conditions: 10 g of composition per 100 ml of pure demineralised water, at a temperature of 18° C.,
it is non-caking,
its pourability index is greater than about 80, and ranges from about 80 to about 85, particularly from about 81 to about 82, measured according to the Hosakawa test, as described in IRON WORKS LTD., Osaka, Japan, and if it is glucose, the pourability index is about 55 to about 70, the specific gravity of the compacted product is about 0.90 to about 1.00, particularly about 0.97 to about 1.00, and the specific gravity of the uncompacted product is about 0.75 to about 0.90, particularly about 0.83 to about 0.87, measured according to the Hosakawa test, and if the said product is glucose, the specific gravity of the compacted product is about 0.70 to about 0.90 and the specific gravity of the uncompacted product is about 0.50 to about 0.70.

The expression "non-caking" means that the crystals do not agglomerate under normal ambient temperature (10 to 30° C.) and humidity (40 to 80%) conditions.

According to another advantageous embodiment of the invention, the composition is characterised in that it contains additional ingredients in a quantity of about 0% to about 10%, and advantageously in a quantity of about 5%, these ingredients being advantageously chosen from heat-sensitive compounds, compounds having food or pharmacological properties, or compounds having a desired taste or colour.

The composition of the invention may be obtained by the process comprising the following steps:
a) a concentrated sucrose syrup with about 60 to about 97, particularly 75% by weight of dry matter is prepared,
b) the pressure is reduced from atmospheric pressure to a value of about 100 to about 300 mbars, particularly about 200 mbars, in order to start evaporating a part of the water contained in the sugar syrup, the rate of evaporation being about 20%,
c) a part of the water contained in the sugar syrup is evaporated under reduced pressure (about 200 mbars) and the syrup is stirred, particularly by mechanical agitation at a peripheral speed of about 100 to about 350 m/min, particularly 200 to 350 m/min, until a coefficient of sugar supersaturation between 1 and 1.3, particularly 1.1 and 1.3 is obtained, and crystallisation is brought about by vigorous agitation of the syrup (in addition to the stirring mentioned above), particularly by mechanical shocks generated by beating by impact, in this supersaturation zone.
d) crystallisation is continued by stopping evaporation and vigorous agitation (beating), and maintaining regular agitation (stirring) for the time required to obtain crystals of the desired size, and advantageously for about 5 min to about 20 min,
e) evaporation is resumed (still whilst stirring the medium at a speed of about 100 to about 250 m/min) until crystals containing less than 1%, particularly less than 0.5% moisture are obtained,
the temperature being kept at a value of about 70° C. to about 100° C. throughout the process, and the pressure being advantageously kept at about 200 mbars during steps c) to e).

According to an advantageous embodiment of the invention, process I is characterised by the following steps:
a) a concentrated sucrose syrup is obtained with about 60 to about 97, particularly 75% by weight of dry matter,
b) the pressure is reduced from atmospheric pressure to a value of about 100 to about 300 mbars, particularly about 200 mbars, in order to start evaporating a part of the water contained in the sugar syrup, the rate of evaporation being about 20%,
c) a part of the water contained in the sugar syrup is evaporated under reduced pressure (about 200 mbars) and the syrup is stirred, particularly by mechanical agitation at a peripheral speed of about 100 to about 350 m/min, particularly 200 to 350 m/min, until a coefficient of sugar supersaturation between 1 and 1.3, particularly 1.1 and 1.3 is obtained, and crystallisation is brought about by vigorous agitation of the syrup (in addition to the stirring mentioned above), particularly by mechanical shocks generated by beating by impact, in this supersaturation zone,
d) crystallisation is continued by stopping evaporation and vigorous agitation (beating), and maintaining regular agitation (stirring) for the time required to obtain crystals of the desired size, and advantageously for about 5 min to about 20 min,
e) evaporation is resumed (still whilst stirring the medium at a speed of about 100 to about 350 m/min, particularly 200 to 350 m/min), until crystals containing less than 1%, particularly less than 0.5% moisture are obtained,
the temperature being kept at a value of about 40° C. to about 100° C., particularly about 70° C. to about 100° C. throughout the process, and the pressure being advantageously kept at about 200 mbars during steps c) to e).

The process of the invention starts with the preparation of the concentrated sugar syrup. The suitable concentration is, by way of example, between 60 and 80% by weight of dry matter. In order to avoid recrystallisation and degradation of the sugar or any other product added to the solution, the temperature is kept at 40° C. to 100° C., particularly 70° C. to 100° C. The pressure is reduced to 100–300 mbars in order to commence evaporation. At the same time, the syrup is kept under agitation. This mechanical agitation or stirring of the syrup is required to homogenise the medium, and is carried out with the aid of an agitation moving part advantageously placed at the bottom of the tank used in the process of the invention. By way of illustration, this stirring may be carried out with a mixer-evaporator, a crystalliser, a mixer-homogeniser, a mixer-blender or any other suitable equipment. It is important that this stirring be vigorous and that the energy applied to the syrup be controlled. Moreover, to ensure that the process operates satisfactorily, the plant must be able to operate under reduced pressure and at a controlled temperature.

Vigorous agitation, advantageously carried out by beating the solution by impact stimulates the formation of nuclei and a haze may be observed after a certain period. These conditions are maintained for a few minutes and then evaporation is stopped. By way of illustration, the tests which are described in the examples of the invention are carried out on a 45 litre Guedu evaporator-mixer fitted, for the purpose of beating by impact, with a mixer or knives, the rate of rotation of which is about 1000 to about 2000 revolutions/min.

Stirring is maintained so as better to control the crystal growth. During the final phase, evaporation is continued with stirring until dry crystals are obtained.

By varying the rate of agitation for stirring the medium, the rate of evaporation and the duration of the various steps, it is possible to prepare crystals with a well defined mean particle size which can be obtained in a reproducible manner.

The composition of the invention may also be obtained by a process comprising the following steps:
a) a concentrated syrup is prepared,
b) the syrup is evaporated under pressure with vigorous agitation in the crystallisation zone until crystals appear, the temperature and the rate of evaporation being controlled until a dry matter content of about 80% to about 90% is obtained,
c) evaporation is continued with a reduction in the rate of agitation until a dry product is obtained, the temperature being kept constant with respect to the previous step, the temperature being adjusted and kept at a given value in the interval from about 40° C. to about 100° C., and particularly from about 70° C. to about 100° C., during steps a) to c) described above.

The composition of the invention may also be obtained in the following manner:
a) a concentrated sugar syrup is prepared with about 60% to about 97%, particularly about 75% by weight of dry matter,
b) evaporation of the syrup is brought about by reducing the pressure so as to achieve boiling of this syrup at the chosen temperature,
c) the syrup is stirred particularly by mechanical agitation at a peripheral speed of about 100 to about 350 m/min, particularly 200 to 350 m/min, the coefficient of supersaturation of the syrup being between 1 and 1.3, particularly 1.1 and 1.3, and crystallisation is brought about by vigorous agitation of the syrup (in addition to the stirring mentioned above), particularly by mechanical shocks generated by beating by impact, in this supersaturation zone,
d) evaporation is continued under the same temperature and pressure conditions as those used in the previous steps, until a medium is obtained of which the crystals constitute the majority phase (more than about 50%, and particularly more than about 70% with respect to the medium),
the rate of agitation being reduced by about 50 to about 200 m/min, the temperature being kept constant with respect to the previous steps, beating being maintained until a dry product is obtained, composed of crystals of the desired size, containing less than 1%, particularly less than 0.5% of moisture,
the temperature being adjusted and kept at a constant value within the range from about 40° C. to about 100° C., particularly about 70° C. to about 100° C., throughout the duration of the steps.

The invention also relates to a process for the preparation of the compositions described above, said process being characterised by the following steps:
a) a concentrated syrup is prepared,
b) the syrup is evaporated under pressure with vigorous agitation in the crystallisation zone until crystals appear, the temperature and the rate of evaporation being controlled until a dry matter content of about 80% to about 90% is obtained,
c) evaporation is continued with a reduction in the rate of agitation until a dry product is obtained, the temperature being kept constant with respect to the previous step,
the temperature being adjusted and kept at a given value in the interval from about 40° C. to about 100° C., and particularly from about 70° C. to about 100° C., during steps a) to c) described above.

This process will be designated hereinafter by "process II".

According to an advantageous embodiment of the invention, process II is characterised by the following steps:
a) a concentrated sugar syrup is prepared with about 60% to about 97%, particularly 75% by weight of dry matter,
b) evaporation of the syrup is brought about by reducing the pressure so as to achieve boiling of this syrup at the chosen temperature,
c) the syrup is stirred particularly by mechanical agitation at a peripheral speed of about 100 to about 350 m/min, particularly 200 to 350 m/min, the coefficient of supersaturation of the syrup being between 1 and 1.3, particularly 1.1 and 1.3, and crystallisation is brought about by vigorous agitation of the syrup (in addition to the stirring mentioned above), particularly by mechanical shocks generated by beating by impact, in this supersaturation zone,
d) evaporation is continued under the same temperature and pressure conditions as those used in the previous steps, until a medium is obtained of which the crystals constitute the majority phase (more than about 50%, and particularly more than about 70% with respect to the medium),
the rate of agitation being reduced by about 50 to about 200 m/min, the temperature being kept constant with respect to the previous steps, beating being maintained until a dry product is obtained, composed of crystals of the desired size, containing less than 1%, particularly less than 0.5% of moisture,
the temperature being adjusted and kept at a constant value within the range from about 40° C. to about 100° C., particularly about 70° C. to about 100° C., throughout the duration of the steps.

Process II starts with the preparation of the concentrated sugar syrup. The suitable concentration is, by way of example, between 60 and 80% by weight of dry matter. In order to avoid recrystallisation and degradation of the sugar or any other product added to the solution, the temperature is kept at 40° C. to 100° C., particularly 70° C. to 100° C. The syrup is kept under agitation and the pressure is reduced so as to achieve boiling of the syrup at the chosen temperature. The mechanical agitation or stirring of the syrup is required to homogenise the medium, and is carried out with the aid of an agitation moving part advantageously placed at the bottom of the tank used in the process of the invention. By way of illustration, this stirring may be carried out with a mixer-evaporator, a crystalliser, a mixer-homogeniser, a mixer-blender or any other suitable equipment. It is important that this stirring be vigorous and that the energy applied to the syrup be controlled. Moreover, to ensure that the process operates satisfactorily, the plant must be able to operate under reduced pressure and at a controlled temperature.

Vigorous agitation, advantageously carried out by beating and impact of the solution, stimulates the formation of nuclei and a haze may be observed after a certain period.

Concentration of the syrup is carried out with a rate of evaporation between 20 and 30% per hour of the initial quantity of water. Evaporation is carried out under reduced pressure, the pressure being defined by the temperature of the syrup in order to obtain boiling of the medium at this temperature.

The system is kept in this state of equilibrium of rate of evaporation/pressure/temperature until a rate of evaporation of about 65%.

The medium then becomes very pasty and, in this second step, the rate of agitation of the moving part is lowered to 190 m/min (peripheral speed) and evaporation is continued with a gradually decreasing pressure in order to maintain a constant temperature until a dry powder is obtained.

With respect to process I, process II has the following differences:
suppression of step d): "stopping evaporation and maintaining agitation for a certain period",
process II is advantageously applied to industrial trials.

The examples presented illustrate the application of the process of the invention permitting the production of compositions of sugar crystals having an average size between 80 and 150 $\mu$m (Examples 1 and 2). Moreover, an example describes the use of the process for obtaining sugar crystals containing a second compound, namely caramel (Example 3).

Examples 4 to 6 describe respectively the preparation of glucose, lactose and erythritol according to the invention.

Example 7 corresponds to an industrial trial.

The present invention describes a microcrystalline sugar composition, the mean aperture of which is centred around 20 to 220 μm, particularly 20 to 200 μm. The size distribution of the crystals around the mean value is of the Gaussian type, with a CV between 20% and 50% and its uniformity index is between 1 and 5. The crystals, regular in shape, are not agglomerates. The crystals have a high density. The product is free-flowing and dissolves rapidly in water. The crystals obtained by this method do not require any particular sieving other than the removal of agglomerates and particles greater than 300 μm representing less than 10% of the composition. Tile powder is obtained with a good yield and a Gaussian type distribution or having a uniformity index between 1 and 5. As the process for the preparation of said product is very well controlled, it is possible to obtain crystals with the desired average particle size by modifying only certain parameters. Consequently, the present invention describing compositions of microcrystalline sugar with a specific diameter between 20 and 220 μm and more particularly between 80 and 150 μm is well demonstrated.

The process of the present invention allows the addition of desired ingredients to the sugar, it being possible to carry out the addition within the scope of process I, preferably after the formation of the haze and before evaporation is stopped, for example between step c) and step d).

Within the scope of process II, the addition may be made at the time when supersaturation reaches a value between 1.0 and 1.3.

In this case, co-crystallisation of the sugar with another ingredient is observed. The present invention also describes the microcrystalline sugar with the desired mean particle size doped with (a) chosen ingredient(s). A wide range of ingredients such as gums, emulsifiers, chemicals may be added. The sugar crystals in this case act as a support for the ingredients used, for example as food or pharmaceutical products, either for colour or taste, or for any other desired property.

The present invention consequently describes compositions of sugar microcrystals and other ingredients.

The process described in the present invention allows the use of controlled temperature conditions. Thus, it is possible to add a second heat-sensitive ingredient. The heat-sensitive compounds may be vitamins, amino acids, carotenoids, antibiotics.

The crystals obtained by the present invention have regular shapes and are not agglomerated, as FIG. 1 shows. Generally speaking, in the examples that follow, the mean aperture of the crystals is centred around a well defined value and this is not the case in the processes described by the prior art. The following examples illustrate the invention and are in no way interpreted as limiting the process.

BRIEF DESCRIPTION OF THE DRAWINGS

FIG. 1 A represents a photograph of a microcrystalline sugar composition of 80 μm observed under an electron microscope, magnification X50.

FIG. 1B represents a photograph of a microcrystalline sugar composition of 80 μm observed under an electron microscope, magnification X150.

FIG. 1C represents a photograph of a commercial icing sugar observed under an electron microscope, magnification X50.

FIG. 2 represents the rate of dissolution of sugars in pure water at 18° C. The time corresponding to total dissolution (expressed in seconds) is plotted on the axis of the abscissas. The various sugars tested are plotted on the axis of the ordinates, it being recalled that the icing sugar has a particle size of 80 to 100 μm, that the high quality sugar has a particle size of 200 to 250 μm, and that the sugars with a respective particle size of 150 μm and 80 μm correspond to the compositions of the invention.

Products in powder form may form agglomerates in the storage tanks and feed hoppers. Emptying these tanks and other hoppers is made difficult by this phenomenon, leading to the formation of arches (blocks of powder remaining stuck to the walls of the hoppers and above a cavity, and forming dead spots), disturbing the flow of the powder by simple gravity. It is necessary, therefore, to use any mechanical device that will allow this powder to be kept in homogeneous mixture, by storing it under agitation, or by drawing it off from the hopper using rotating sluices or vibrators.

The difficulty of handling a product in powder form is reflected in its pourability index which may range from 0 (product with a high agglomeration capacity, caking, sticky) to 100 (extremely free-flowing product which behaves like a liquid).

Low indices require special equipment adapted to each case; high indices do not pose any particular storage and handling problem.

Figure 1D:
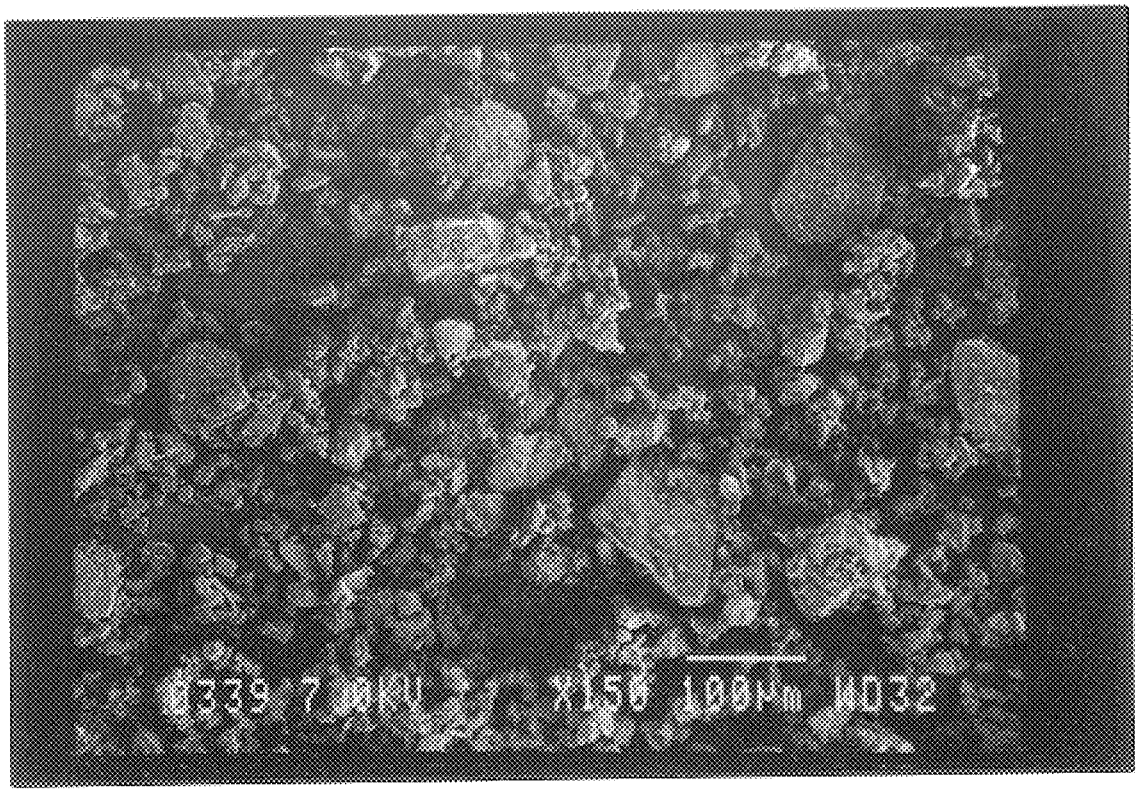
FIG. 1D represents a photograph of a commercial icing sugar observed under an electron microscope, magnification X150.
Figure 3:
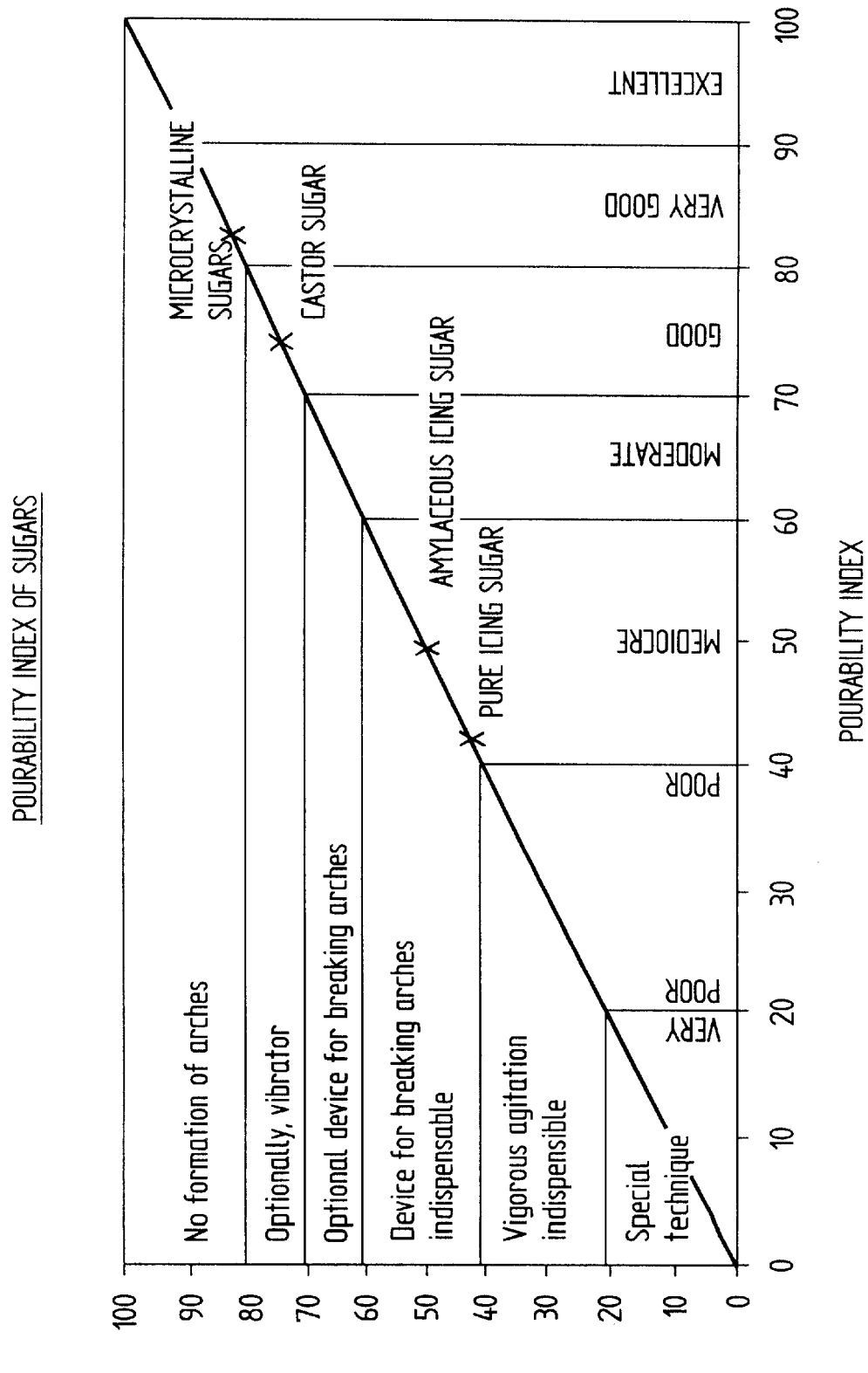
FIG. 3 represents the pourability index.
Figure 4:
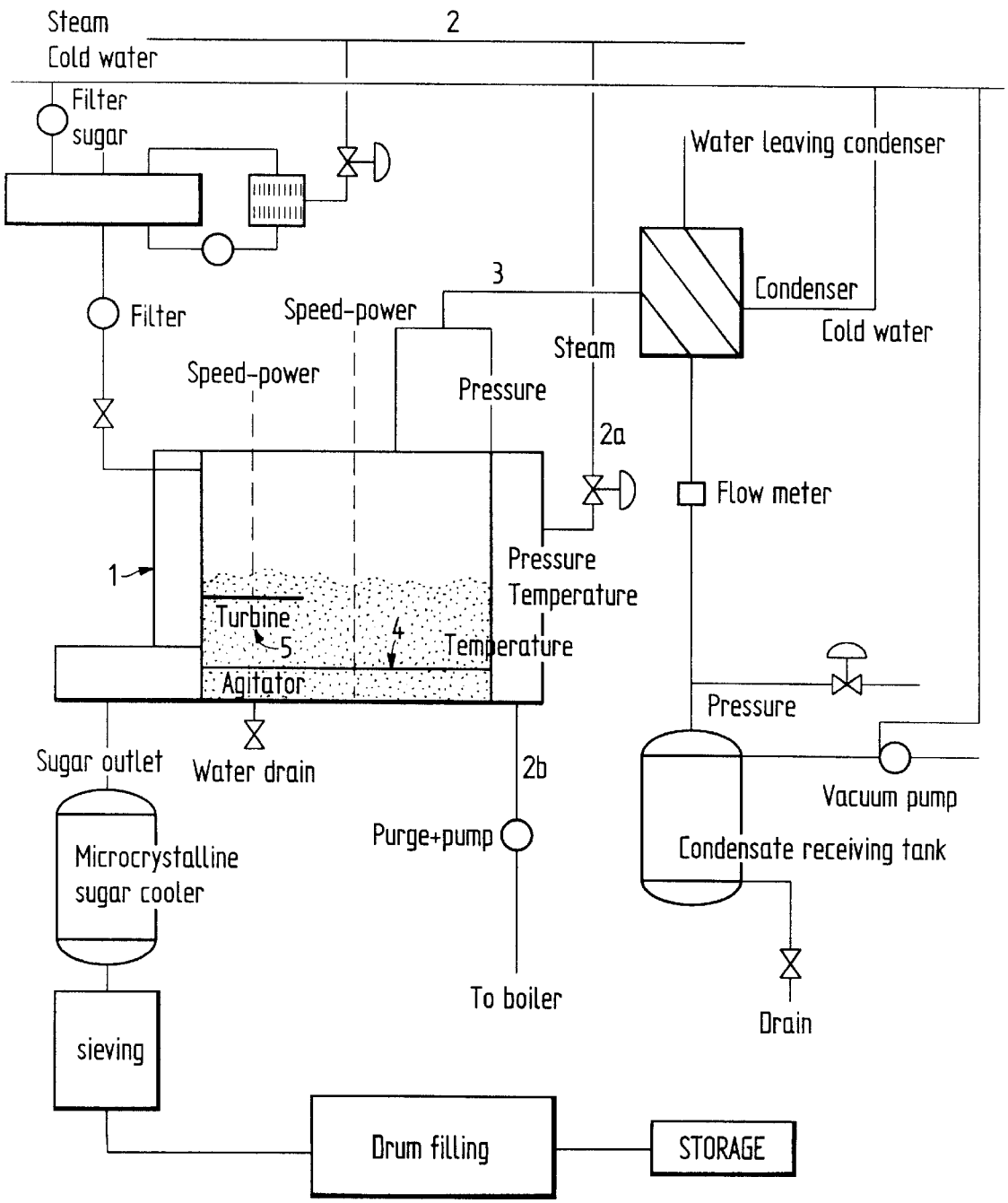

FIG. 4 represents a functional diagram of the apparatus used in connection with Examples 1 to 7.

The apparatus used may be composed of an evaporator-mixer composed of a vessel (1) capable of operating under reduced pressure and at a controlled temperature. To this end, this vessel contains a heat exchange fluid (2), the inlet port of which is, for example in 2a and the outlet port in 2b, and it is linked to a vacuum point (3).

Mixing (or stirring) of the sugar syrup during the process is carried out by an agitator moving part (4).

Beating by impact is carried out, for example, by a telescopic lump breaker knife (5).

EXAMPLE 1

Preparation of microcrystalline sugar with a mean aperture of 80 μm and a CV=40%.

Twenty kg of sugar are dissolved in 6 kg of water at 80° C., which temperature will be kept constant throughout the preparation.

The rate of stirring is fixed at 245 m/min (peripheral speed). Evaporation of the syrup is carried out until a supersaturation value between 1.1 and 1.3 and advantageously 1.2, and the action of the lump remover (about 1000 rpm) is effective as soon as the defined supersaturation value is reached. The rate of evaporation is kept at a value of 1.5 l/h under 250 mbars.

After 15 min under these conditions, a white haze signifying nucleation appears in the medium. This state is maintained for 40 min, the action of the lump remover allowing the number of nuclei to multiply by limiting their growth.

Evaporation and beating are stopped for 10 minutes, giving way to a phase of regular crystal growth.

In the last step, the rate of agitation of the stirring moving part is fixed at 190 m/min (peripheral speed) and evaporation is continued at an increasing rate until a dry powder is obtained.

Overall duration of the operation: 3 hours.

The composition of the invention thus obtained has the following properties:
Rate of dissolution: 7 sec
Pourability index: 81
Specific gravity of compacted composition: 0.97
Specific gravity of uncompacted composition: 0.83

EXAMPLE 2

Preparation of microcrystalline sugar with a mean aperture of 150 μm and a CV=30%.

Twenty kg of sugar are dissolved in 6 kg of water at 80° C., which temperature will be kept constant throughout the operation.

The rate of agitation of the stirring moving part is fixed at 135 m/mn (peripheral speed). Evaporation of the syrup is carried out until a supersaturation value between 1.1 and 1.3 and advantageously 1.2, and the action of the lump remover (about 1000 rpm) is effective as soon as the defined supersaturation value is reached.

The rate of evaporation is kept at a value of 1.5 l/h under 250 mbars.

After 10 min under these conditions, a white haze which signifies nucleation appears in the medium. This state is maintained for 5 min. then evaporation and the lump remover are stopped for 15 minutes, promoting the phase of crystal growth.

In the second step, the rate of agitation of the stirring moving part is fixed at 135 m/min (peripheral speed) and evaporation is continued at an increasing rate until a dry powder is obtained.

Overall duration of the operation: 5 hours.

The composition of the invention thus obtained has the following properties:
Rate of dissolution: 9 sec
Pourability index: 82
Specific gravity of compacted composition: 1.00
Specific gravity of uncompacted composition: 0.87

EXAMPLE 3

Preparation of microcrystalline sugar with a mean aperture of 150 μm and a CV=30% containing caramel.

Twenty kg of sugar are dissolved in 6 kg of water at 80° C., which temperature will be kept constant throughout the operation.

The rate of agitation of the stirring moving part is fixed at 135 m/mn (peripheral speed). Evaporation of the syrup is carried out until a supersaturation value between 1.1 and 1.3 and advantageously 1.2, and the action of the lump remover (about 1000 rpm) is effective as soon as the defined supersaturation value is reached.

The rate of evaporation is kept at a value of 1.5 l/h under 250 mbars.

At this moment, 400 g of aromatic caramel representing 2% of the total mass of sugar are diluted in the medium.

After 5 minutes' homogenisation, evaporation and the lump remover are stopped for 15 minutes, promoting the phase of crystal growth.

In the last step, the rate of agitation of the stirring moving part is fixed at 135 m/min (peripheral speed) and evaporation is continued at an increasing rate until a dry powder is obtained.

Overall duration of the operation: 5 hours.

The composition of the invention thus obtained has the same characteristics as the composition obtained in Example 2.

EXAMPLE 4:

Preparation of microcrystalline glucose with a mean aperture of 75 μm.

Eighteen kg of glucose are dissolved in 5.4 kg of water at 70° C., which temperature will be kept constant throughout the operation.

The rate of agitation of the stirring moving part is fixed at 245 m/min (peripheral speed).

Evaporation of the syrup is carried out until a supersaturation value between 1.1 and 1.4 and advantageously 1.3, and the action of the lump remover (about 1000 rpm) is effective as soon as the defined supersaturation value is reached. The rate of evaporation is kept at a mean value of 1.5 l/h under about 180 mbars.

After 100 min under these conditions, a white haze signifying nucleation appears in the medium. This state is maintained for 40 min, the action of the lump remover allowing the number of nuclei to multiply by limiting growth.

Evaporation and beating are stopped for 10 minutes, promoting the phase of crystal growth.

In the second step, the rate of agitation of the moving part is fixed at 140 m/min (peripheral speed) and evaporation is continued at an increasing rate until a dry powder is obtained.

Overall duration of the operation: 4 hours.

The composition of the invention thus obtained has the following properties:
pourability index: 60
specific gravity of the compacted composition: 0.75
specific gravity of the uncompacted composition: 0.52

EXAMPLE 5

Preparation of microcrystalline lactose with a mean aperture of 50 μm.

Fifteen kg of lactose are dissolved in 20 kg of water at 72° C., which temperature will be kept constant throughout the operation.

The rate of agitation of the stirring moving part is fixed at 245 m/min (peripheral speed).

Evaporation of the syrup is carried out until a supersaturation value between 1.1 and 1.3 and advantageously 1.1, and the action of the lump remover (about 1000 rpm) is effective as soon as the defined supersaturation value is reached. The rate of evaporation is kept at a mean value of 2.5 l/h under about 180 mbars.

After 220 min under these conditions, a white haze signifying nucleation appears in the medium. This state is maintained for 40 min, the action of the lump remover allowing the number of nuclei to multiply by limiting growth.

Evaporation and beating are stopped for 10 minutes, promoting the phase of crystal growth.

In the second step, the rate of agitation of the moving part is fixed at 140 m/min (peripheral speed) and evaporation is continued at an increasing rate until a dry powder is obtained.

Overall duration of the operation: 7 hours.

The composition of the invention thus obtained has the following properties:

pourability index: 80
specific gravity of the compacted composition: 0.93
specific gravity of the uncompacted composition: 0.83

EXAMPLE 6

Preparation of microcrystalline erythritol with a mean aperture of 220 μm.

Eighteen kg of erythritol are dissolved in 8 kg of water at 70° C., which temperature will be kept constant throughout the operation.

The rate of agitation of the stirring moving part is fixed at 245 m/min (peripheral speed).

Evaporation of the syrup is carried out until a supersaturation value between 1.1 and 1.3 and advantageously 1.1, and the action of the lump remover (about 1000 rpm) is effective as soon as the defined supersaturation value is reached. The rate of evaporation is kept at a mean value of 2.0 l/h under about 180 mbars.

After 40 min under these conditions, a white haze signifying nucleation appears in the medium.

Evaporation and beating are stopped for 10 minutes, promoting the phase of crystal growth.

In the second step, the rate of agitation of the moving part is fixed at 140 m/min (peripheral speed) and evaporation is continued at an increasing rate until a dry powder is obtained.

Overall duration of the operation: 3.5 hours.

The action of the lump remover (about 1000 rpm) is effective as soon as evaporation starts and throughout the operation. Concentration of the syrup is carried out at a mean rate of evaporation of 20 to 30% /hour. The energy brought into the system (steam heating, double jacket) is controlled by the predetermined flow rate set point.

Evaporation is carried out under reduced pressure, the pressure defined by the temperature of the syrup in order to obtain boiling of the medium at this temperature.

The system is kept in this state of equilibrium of rate of evaporation/pressure/temperature until a rate of evaporation of about 65%.

The medium then becomes very pasty and, in this second step, the rate of agitation of the moving part is lowered to 190 m/min (peripheral speed) and evaporation is continued with a gradually decreasing pressure in order to keep a constant temperature until a dry powder is obtained.

At the end of the cycle, the product is discharged without prior cooling, any lumps present in the powder are removed by rapid passage through a 300 μm sieve. The crystals obtained do not cake after several days' storage in ambient air.

Overall duration of the operation: 6 hours.

The composition of the invention thus obtained has the following properties:
rate of dissolution: 8 sec
pourability index: 82
density of the compacted composition: 0.98
density of the uncompacted composition: 0.84.

|  | Icing sugar | High quality caster sugar | Comparative example Example 1 Sucrose | Example 2 Sucrose | Example 3 Sucrose | Example 4 Glucose | Example 5 Lactose | Example 6 Erythritol | Example 7 Sucrose |
|---|---|---|---|---|---|---|---|---|---|
| MA (μm) | <80 | 250 | 80 | 150 | 150 | 75 | 50 | 220 | 120 |
| CV (%) | ND* | ND* | 35–45 | 30–40 | 30–40 | ND* | ND* | ND* | 50 |
| Pourability index | 42 | 75 | 81 | 82 | 82 | 60 | 80 | 83 | 82 |
| Rate of dissolution (sec) | 22** | 13 | 7 | 9 | 9 | ND* | ND* | ND* | 8 |
| Density of uncompacted product | 0.45 | 0.65 | 0.83 | 0.87 | 0.87 | 0.52 | 0.83 | 0.90 | 0.84 |
| Density of compacted product | 0.88 | 0.87 | 0.97 | 1.00 | 1.00 | 0.75 | 0.93 | 0.92 | 0.98 |
| Caking | Yes | No caking | No caking | No caking | No caking | No caking | No caking | No caking | No caking |

*ND: not determined
**problem of wettability

The composition of the invention thus obtained has the following properties:
rate of dissolution: insoluble under the test conditions (persistent turbidity)
pourability index: 83
density of the compacted composition: 0.92
density of the uncompacted composition: 0.90

EXAMPLE 7

Industrial trial

Preparation of microcrystalline sucrose with a mean aperture of 120 μm.

In a 1600 litre Guedu mixer, 800 kg of sucrose are dissolved in 310 kg of water at 62° C., which temperature will be kept constant throughout the operation.

The rate of agitation of the stirring moving part is fixed at 330 m/min (peripheral speed).

We claim:

1. A composition containing sugar microcrystals, wherein the crystals are essentially unbroken monocrystals with a regular geometric shape, homogeneous with respect to one another, and the particle size follows a Gaussian distribution whose median is about 20 μm to about 220 μm, the coefficient of variation being about 20% to about 50%; or the particle size distribution has a uniformity index between 1 and 5.

2. The composition according to claim 1, wherein:

the particle size follows a Gaussian distribution whose median ranges from about 20 μm to about 200 μm, the coefficient of variation being about 30% to 40%; or the particle size distribution has a uniformity index between 2.5 and 3.5.

3. The composition according to claim 1, wherein the composition has the following properties:
- its rate of dissolution ranges from about 5 to about 10 seconds, under the following conditions: 10 g of composition per 100 ml of pure demineralized water at a temperature of 18° C.;
- it is non caking;
- its pourability index is greater than about 80, and ranges from about 80 to about 85, measured according to the Hosakawa test as described in IRON WORKS LTD, Osaka, Japan, and if it is glucose, the pourability index is about 55 to about 70;
- the specific gravity of the compacted product ranges from about 0.90 to about 1.00, and the specific gravity of the uncompacted product ranges from about 0.75 to about 0.90, measured according to the Hosakawa test, and if the product is glucose, the specific gravity of the compacted product is about 0.70 to about 0.90 and the specific gravity of the uncompacted product is about 0.50 to about 0.70.

4. The composition according to claim 3, wherein the rate of dissolution ranges from about 7 to about 9 seconds; the pourability index ranges from about 81 to about 82; the specific gravity of the compacted product ranges from about 0.97 to about 1.00; and the specific gravity of the uncompacted product ranges from about 0.83 to about 0.87.

5. The composition according to claim 1, wherein the composition contains additional ingredients in a quantity of about 0% to about 10%, said ingredients being selected from the group consisting of heat-sensitive compounds, compounds having food or pharmacological properties, and compounds having a desired taste or color.

6. The composition according to claim 5, wherein the quantity of additional ingredients is about 5%.

7. The composition according to claim 1, obtained by a process comprising the following steps:
a) preparing a concentrated sucrose syrup containing about 60 to about 97% by weight of dry matter;
b) reducing the pressure from atmospheric pressure to a value of about 100 to about 300 mbars, in order to start evaporating part of the water contained in the sugar syrup, at an evaporation rate of about 20%;
c) evaporating a part of the water contained in the sugar syrup under reduced pressure and stirring the syrup by mechanical agitation at a peripheral speed of about 100 to about 350 m/mn until a coefficient of supersaturation of sugar between 1.1 and 1.3, and crystallization is brought about by vigorous agitation of the syrup;
d) continuing crystallization by stopping evaporation and vigorous agitation, and maintaining mechanical agitation for a time required to obtain crystals of a desired size;
e) resuming evaporation while stirring the medium at a speed of about 100 to 350 m/min until crystals containing less than 1% of moisture are obtained; and
wherein the temperature is kept at a value of about 70° C. to about 100° C. throughout the process, and the pressure is kept at about 200 mbars during steps c) to e).

8. The composition according to claim 1, obtained by a process comprising the following steps:
a) preparing a concentrated sugar syrup containing about 60% to about 97% by weight of dry matter;
b) bringing about evaporation of the syrup by reducing the pressure so as to achieve boiling of the syrup at a chosen temperature;
c) stirring the syrup by mechanical agitation at a peripheral speed of about 100 to about 350 m/min, the coefficient of supersaturation of the syrup being between 1 and 1.3, and bringing about crystallization by vigorous agitation of the syrup;
d) continuing evaporation under the same temperature and pressure conditions as those used in the previous steps, until a medium is obtained in which the crystals constitute more than 50% with respect to the medium;
wherein the rate of mechanical agitation is reduced by about 50 to about 200 m/min, the vigorous agitation is maintained until a dry product is obtained comprised of crystals of a desired size containing less than 1% of moisture, and the temperature is adjusted and kept at a constant value within the range from about 40° C. to about 100° C. throughout the duration of the steps.

9. A process for the preparation of a composition according to claim 1, comprising the following steps:
a) preparing a concentrated sucrose syrup containing about 60 to about 97% by weight of dry matter;
b) reducing the pressure from atmospheric pressure to a value of about 100 to about 300 mbars, in order to start evaporating part of the water contained in the sugar syrup, at an evaporation rate of about 20%;
c) evaporating a part of the water contained in the sugar syrup under reduced pressure and stirring the syrup by mechanical agitation at a peripheral speed of about 100 to about 350 m/mn until a coefficient of supersaturation of sugar between 1.1 and 1.3, and crystallization is brought about by vigorous agitation of the syrup;
d) continuing crystallization by stopping evaporation and vigorous agitation, and maintaining mechanical agitation for a time required to obtain crystals of a desired size;
e) resuming evaporation while stirring the medium at a speed of about 100 to 350 m/min until crystals containing less than 1% of moisture are obtained; and
wherein the temperature is kept at a value of about 70° C. to about 100° C. throughout the process, and the pressure is kept at about 200 mbars during steps c) to e).

10. The process according to claim 9, wherein the prepared syrup contains about 75% by weight of dry matter; the pressure in step b) is reduced to about 200 mbars; the vigorous agitation in step c) is achieved by mechanical shocks generated by beating; the mechanical agitation in step d) is maintained for about 5 to about 20 minutes; and the crystals obtained in step e) contain less than 0.5% of moisture.

11. A process for the preparation of a composition according to claim 1, comprising the following steps:
a) preparing a concentrated sugar syrup containing about 60% to about 97% by weight of dry matter;
b) bringing about evaporation of the syrup by reducing the pressure so as to achieve boiling of the syrup at a chosen temperature;
c) stirring the syrup by mechanical agitation at a peripheral speed of about 100 to about 350 m/min, the coefficient of supersaturation of the syrup being between 1 and 1.3, and bringing about crystallization by vigorous agitation of the syrup;
d) continuing evaporation under the same temperature and pressure conditions as those used in the previous steps, until a medium is obtained in which the crystals constitute more than 50% with respect to the medium;

wherein the rate of mechanical agitation is reduced by about 50 to about 200 m/min, the vigorous agitation is maintained until a dry product is obtained comprised of crystals of a desired size containing less than 1% of moisture, and the temperature is adjusted and kept at a constant value within the range from about 40° C. to about 100° C. throughout the duration of the steps.

12. The process according to claim 11, wherein the prepared syrup contains about 75% by weight of dry matter; the peripheral speed is about 200 to about 350 m/min; the coefficient of supersaturation of the syrup ranges between 1.1 and 1.3; the vigorous agitation in step c) is achieved by mechanical shocks generated by beating; the crystals in step d) constitute more than about 70% with respect to the medium and contain less than 0.5% of moisture; and the temperature is kept constant within the range of about 70° C. to about 100° C. throughout the duration of the steps.

* * * * *